US007938815B2

(12) United States Patent
Shoji et al.

(10) Patent No.: US 7,938,815 B2
(45) Date of Patent: May 10, 2011

(54) COVER FOR BEING MOUNTED ON A MULTI-COMPARTMENT INFUSION BAG

(75) Inventors: Hidekatsu Shoji, Tokushima (JP); Kazunari Yoshikawa, Tokushima (JP); Isamu Tateishi, Naruto (JP)

(73) Assignee: Otsuka Pharmaceutical Factory, Inc., Naruto-Shi (JP)

( * ) Notice: Subject to any disclaimer, the term of this patent is extended or adjusted under 35 U.S.C. 154(b) by 484 days.

(21) Appl. No.: 11/992,651

(22) PCT Filed: Sep. 5, 2006

(86) PCT No.: PCT/JP2006/317527

§ 371 (c)(1),
(2), (4) Date: Mar. 27, 2008

(87) PCT Pub. No.: WO2007/040010

PCT Pub. Date: Apr. 12, 2007

(65) Prior Publication Data

US 2009/0131903 A1 May 21, 2009

(30) Foreign Application Priority Data

Sep. 30, 2005 (JP) ................................. 2005-008018
Nov. 4, 2005 (JP) ................................. 2005-009257

(51) Int. Cl.
*A61B 19/00* (2006.01)

(52) U.S. Cl. ......................... 604/410; 604/403; 604/408

(58) Field of Classification Search .................. 604/403, 604/408, 410, 414, 415, 416; 383/210.1; 220/62.22

See application file for complete search history.

(56) References Cited

U.S. PATENT DOCUMENTS 4,286,640 A * 9/1981 Knox et al. .................. 604/404
4,496,046 A 1/1985 Stone et al. .................. 206/219
4,526,404 A 7/1985 Vazquez ......................... 283/79

(Continued)

FOREIGN PATENT DOCUMENTS

CA 1296299 2/1992

(Continued)

OTHER PUBLICATIONS

Supplementary European Search Report dated Oct. 14, 2009.

(Continued)

*Primary Examiner* — Leslie R Deak

(74) *Attorney, Agent, or Firm* — Kratz, Quintos & Hanson, LLP

(57) ABSTRACT

An object of the present device is to provide a cover capable of preventing the administration of unmixed medicaments to a patient. The cover for being mounted on a multi-compartment infusion bag of the present device is a cover for being mounted on a multi-compartment infusion bag including a plurality of compartments partitioned by at least one easily peelable partitioning seal portion which is opened in response to an increase in the internal pressure of at least one of the plurality of compartments induced by pressing said at least one of the plurality of compartments. The cover has a pair of pinch members that pinch at least one of the plurality compartments. The pair of pinch members has engaging elements that engage each other to maintain a pinching state of the pair of pinch members until the pinching state is released in response to an increase in the internal pressure of said at least one of the compartments so that the suspension portion can be used. The pair of pinch members cover a suspension portion in the pinching state for preventing the use of the suspension portion for suspending the infusion bag until said at least one easily peelable sealing partition is opened.

18 Claims, 6 Drawing Sheets

U.S. PATENT DOCUMENTS 4,731,053 A * 3/1988 Hoffman .......................... 604/89
5,257,985 A 11/1993 Puhl .............................. 604/410
2007/0251838 A1 11/2007 Okahisa ........................ 206/221

FOREIGN PATENT DOCUMENTS

EP 1762213 A1 * 3/2007
JP 08-229099 9/1996
JP 2005-218661 8/2005
JP 2005-245983 9/2005
WO WO 2005/053598 A1 6/2005

OTHER PUBLICATIONS

Canadian Office Action dated Jan. 28, 2010.

* cited by examiner

[ fig.1 ]
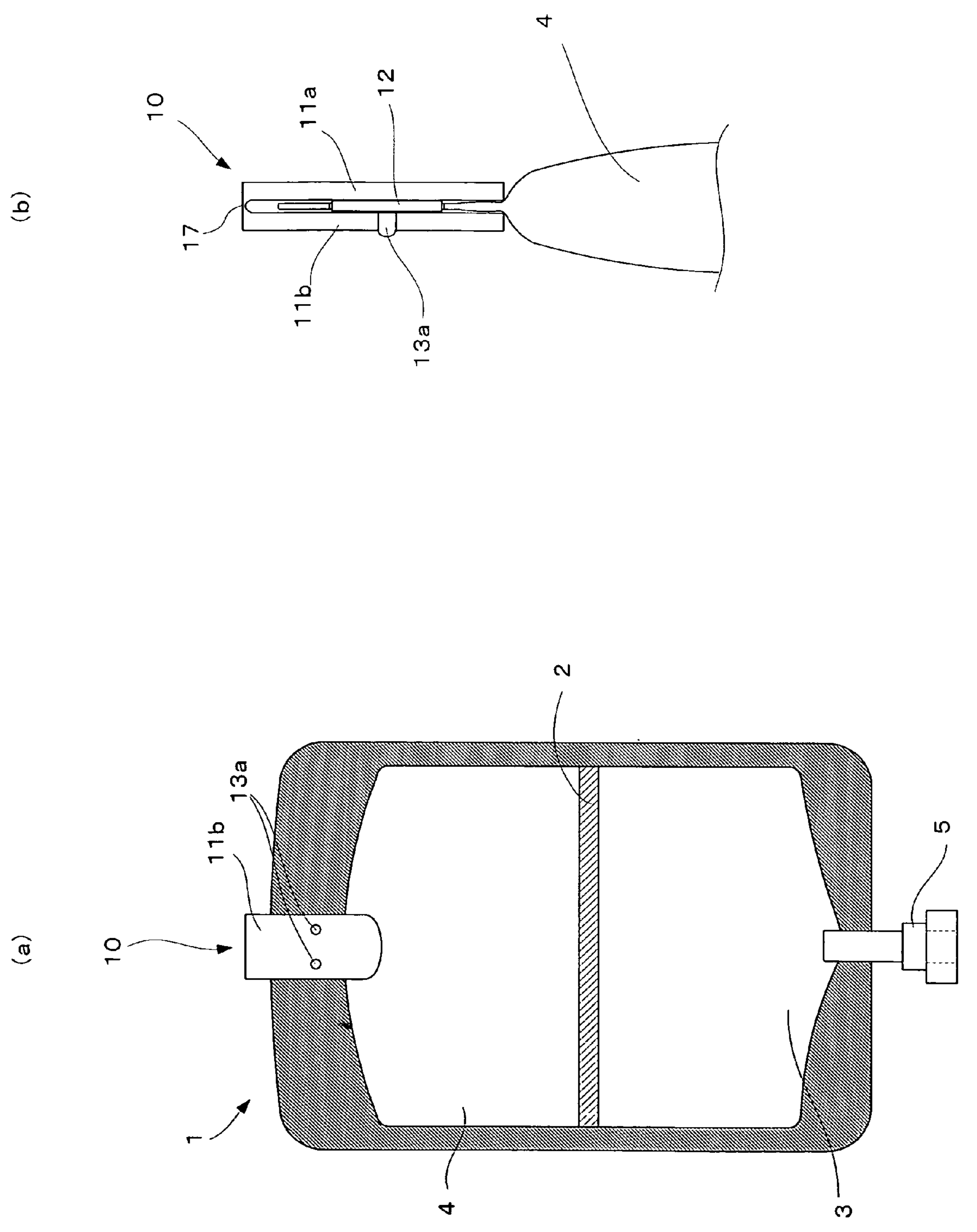

[ fig.2 ]
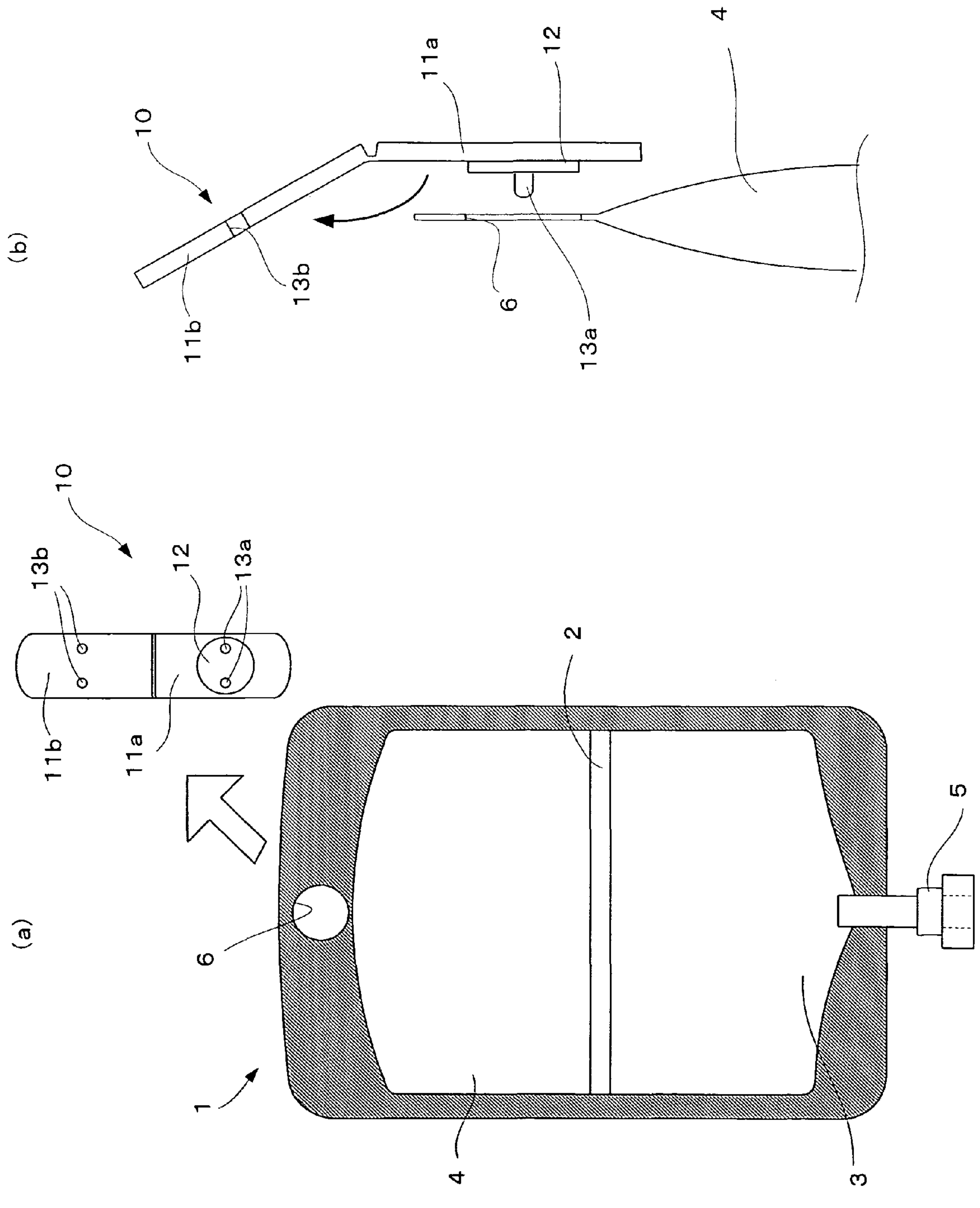

[ fig.3 ]
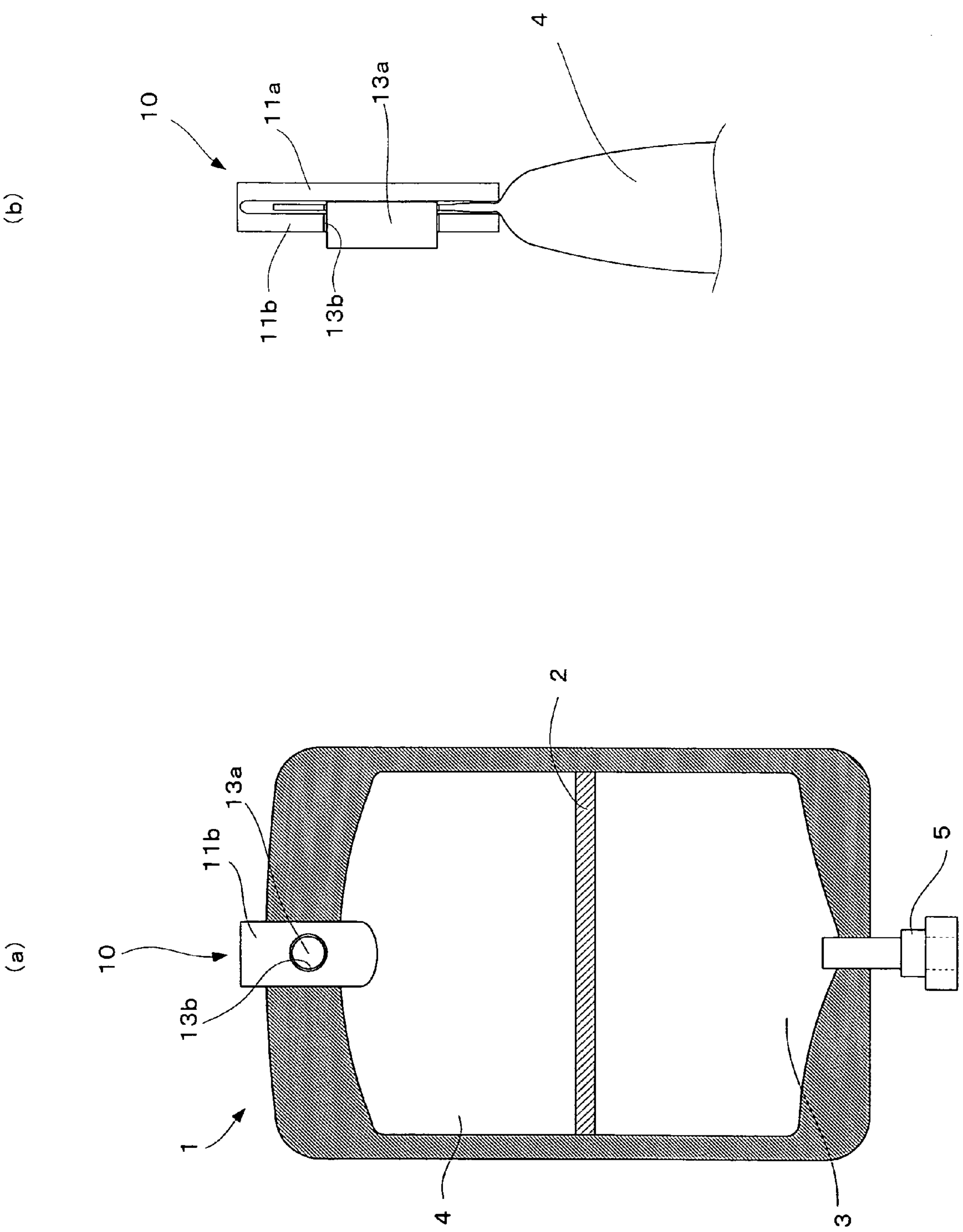

[ fig.4 ]
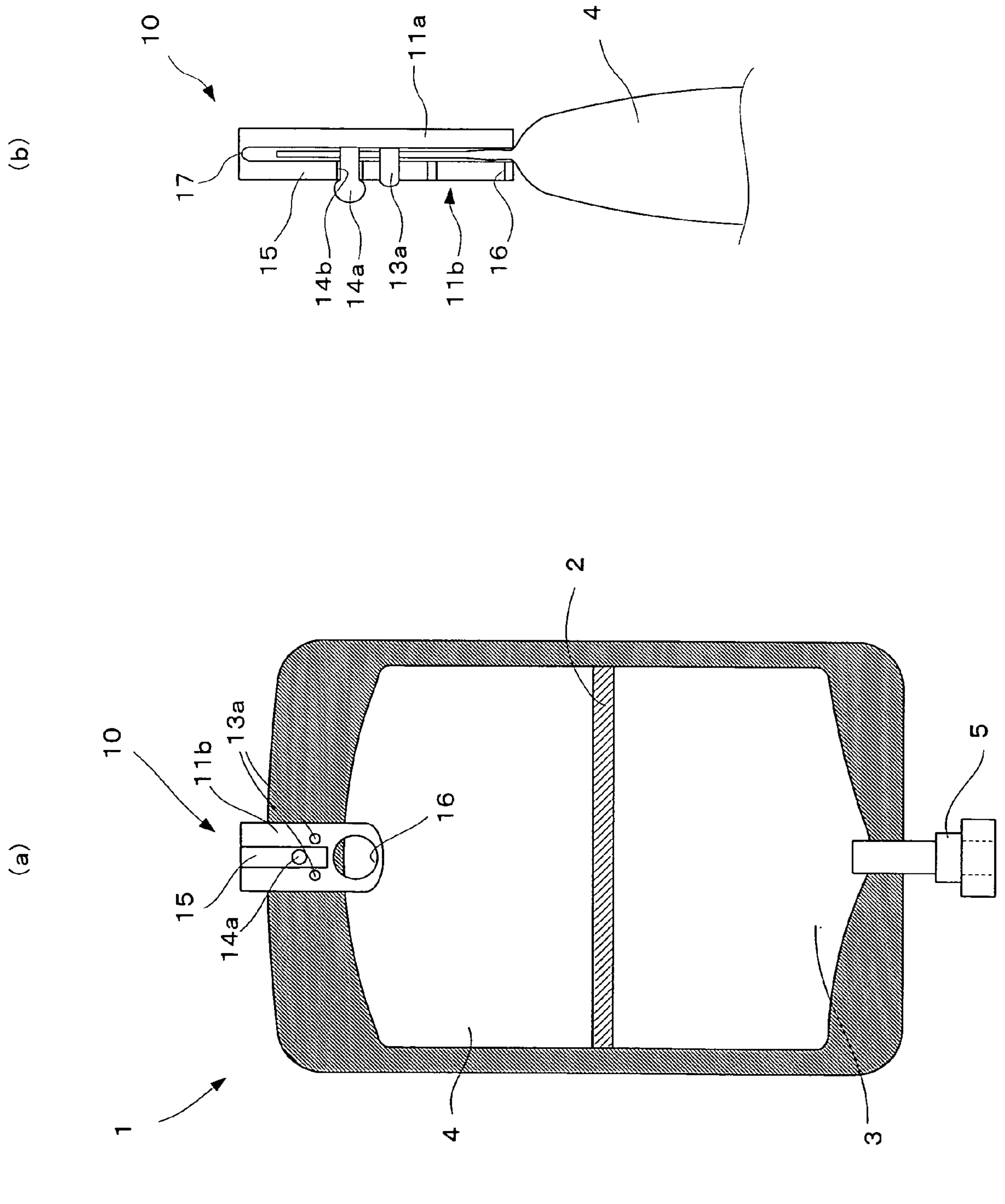

[ fig.5 ]
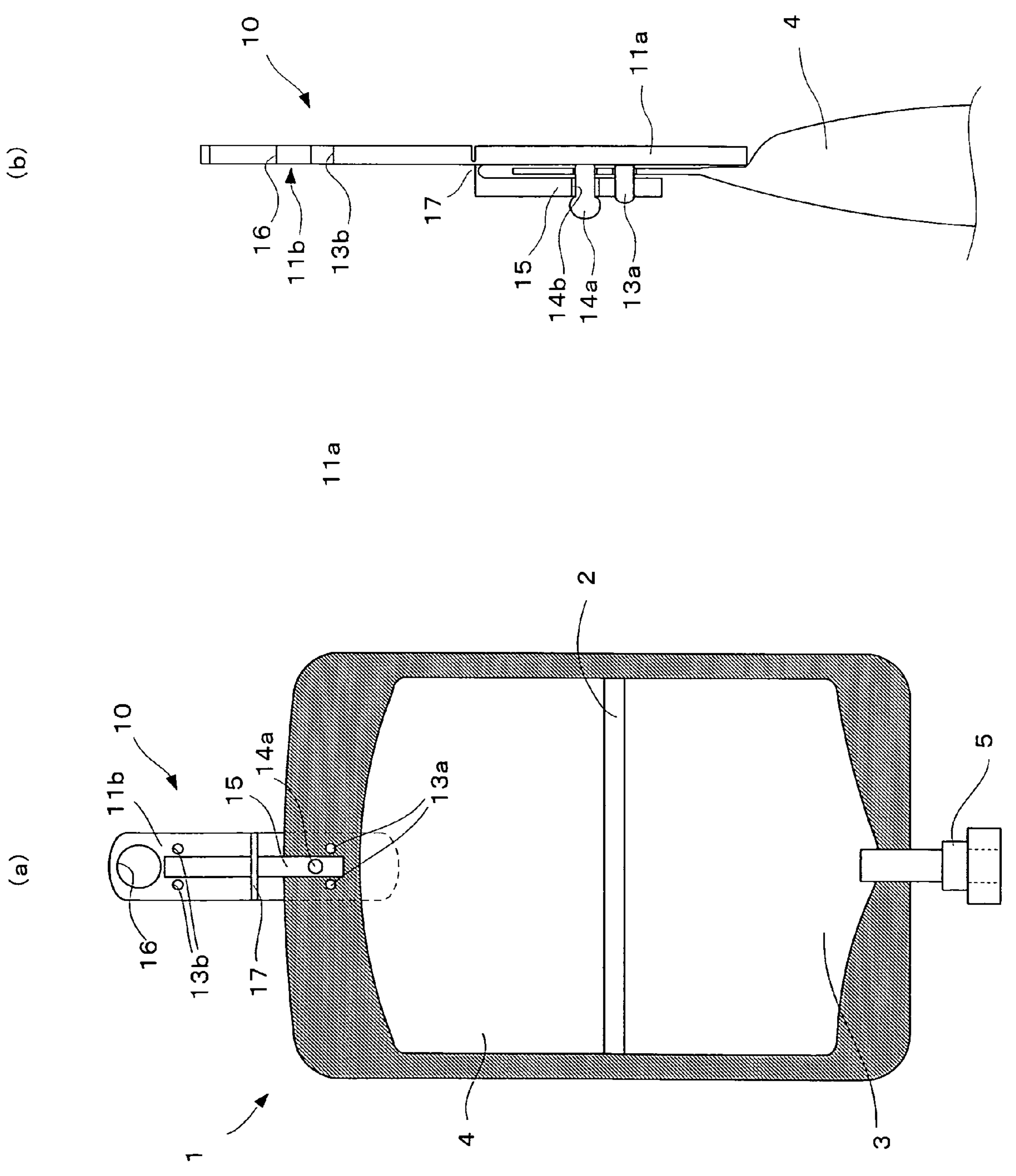

[ fig.6 ]
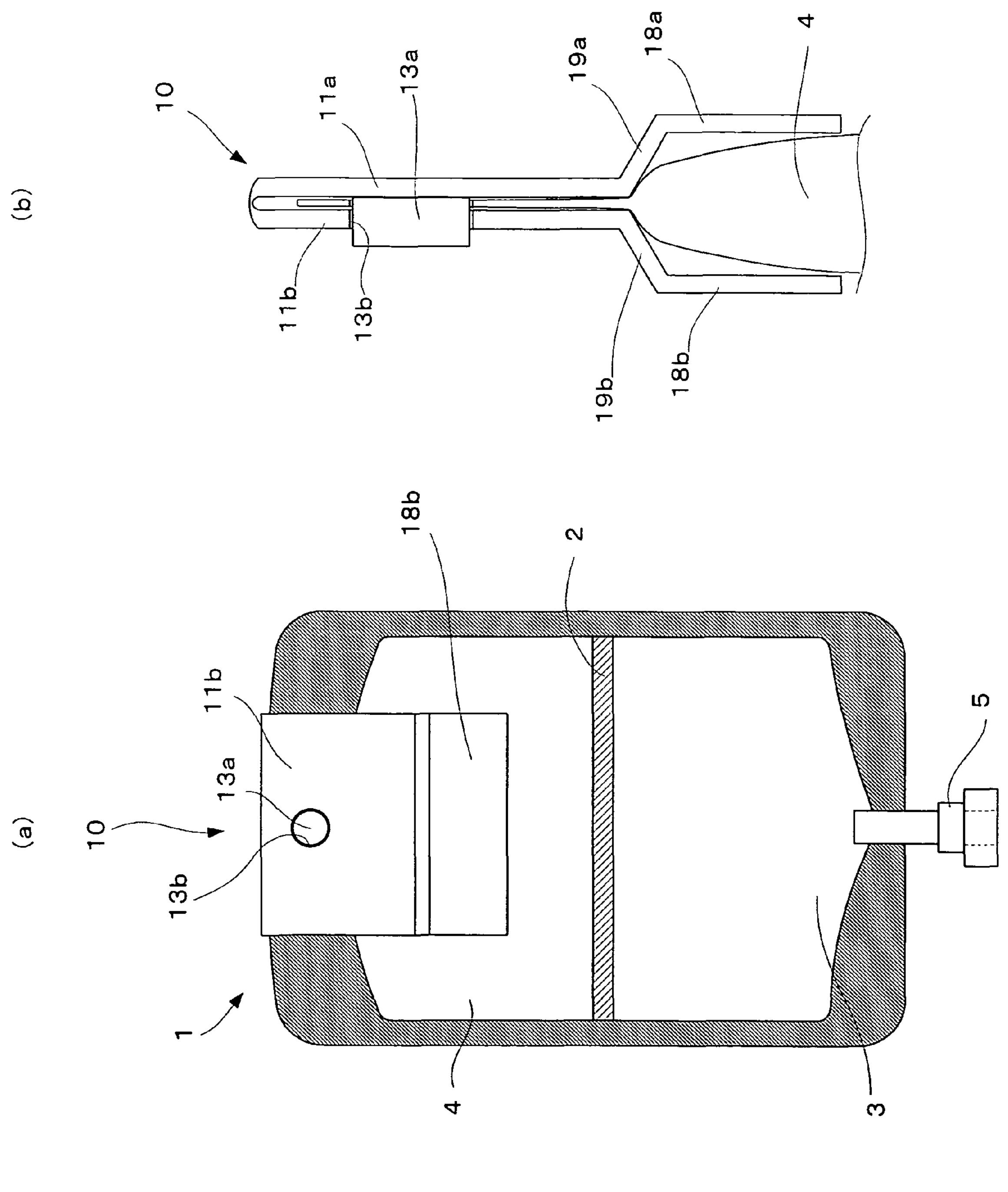

COVER FOR BEING MOUNTED ON A MULTI-COMPARTMENT INFUSION BAG

TECHNICAL FIELD

The present device relates to a cover to be mounted on a multi-compartment infusion bag including a plurality of compartments partitioned by at least one easily peelable partitioning seal portion, for preventing the use of a suspension portion for suspending the infusion bag until said at least one easily peelable partitioning seal portion is opened.

BACKGROUND OF THE INVENTION

Among various medicaments to be administrated to a patient by intravenous injection, some are unstable so that, when premixed, they deteriorate with time. An example of such deterioration with time is the so-called Maillard reaction, which is the browning that occurs during the storage of a mixture of an amino acid infusion and a glucose infusion. Likewise, a mixture of a fat emulsion and an electrolyte solution leads to fat aggregation during storage, and a mixture of a phosphoric acid-containing solution and a calcium-containing solution precipitates calcium phosphate, thereby causing undesirable changes.

For such medicaments, a medical multi-compartment container as follows is often used. Such a medical multi-compartment container has a plastic film body having two compartments for accommodating medicaments, and a medicament outlet portion for releasing a medicament from the body. The two compartments are partitioned by an easily peelable partitioning seal portion formed by heat sealing the inner walls of the body. When used, either of the compartments is pressed at around the center, so that the pressure inside the compartment is increased and the easily peelable partitioning seal portion is thereby opened. The compartments are accordingly communicated, and the two medicaments therein are mixed. The medicament outlet portion is then opened by insertion of an object or the like, and the container is suspended, so as to administer the mixed medicament to a patient (e.g., patent document 1). On the surface of the body of such a container is printed or otherwise displayed an attention-attracting note instructing people not to open the medicament outlet portion by insertion of an object or the like until the easily peelable partitioning seal portion is opened, i.e., before the medicaments are mixed, so as to prevent the administration of unmixed medicaments to a patient.

[Patent Document 1] Japanese Unexamined Patent Publication No. 1996-229099

SUMMARY OF THE DEVICE

Object of the Device

The object of the present device is to provide a cover capable of more efficiently preventing the administration of unmixed medicaments to a patient.

Means for Achieving the Object

To achieve the above object, the cover of the present device is a cover to be mounted on a multi-compartment infusion bag including a plurality of compartments partitioned by at least one easily peelable partitioning seal portion which is opened in response to an increase in the internal pressure of any of the compartments induced by pressing the compartment(s). The cover has a pair of pinch members that pinch at least one of the plurality compartments. The pair of pinch members have engaging elements that engage each other to maintain the pinching state of the pinch members until the pinching state is released in response to an increase in the internal pressure of said at least one of the compartments so that the suspension portion can be used. The pair of pinch members cover a suspension portion in the pinching state for preventing the use of the suspension portion for suspending the infusion bag until said at least one easily peelable sealing partition is opened.

The suspension portion may be formed in the body of the infusion bag. In this case, it is preferable that the cover be capable of being removed from the infusion bag when the pinching state is released, the suspension portion be formed in the body of the infusion bag, and the suspension portion be closed with the pair of pinch members in the pinching state. One of the pinch members may be provided with a seat that fits into the suspension portion. Further, the seat may be provided with at least one engaging projection, and the other pinch member provided with at least one engaging hole that engages with said at least one engaging projection, so that the engaging projection(s) and the engaging hole(s) serve as the engaging elements.

Alternatively, one of the pinch members may also be provided with an engaging projection that fits into the suspension portion, and the other pinch member provided with an engaging hole that engages with the engaging projection, so that the engaging projection and the engaging hole serve as the engaging elements. The pair of pinch members are preferably swingably connected to each other.

The suspension portion may instead be formed in the cover. In this case, it is preferable that one of the pinch members have fixing elements for fixing the one of the pinch members to the infusion bag, the suspension portion be formed in the other pinch member, and the latter pinch member be swingably connected to the former pinch member so that the latter pinch member can be opened and closed with respect to the former pinch member.

The cover may further have a pair of press-preventing members extending from the pair of pinch members over at least said at least one compartment pinched between the pinch members, with the pair of press-preventing members being connected to the pair of pinch members via step portions so that the press-preventing members are disposed apart from each other.

The pair of pinch members are preferably connected by a hinge portion.

Further, to achieve the above object, the infusion bag of the present device is a multi-compartment infusion bag including a plurality of compartments partitioned by at least one easily peelable partitioning seal portion which is opened in response to an increase in the internal pressure of any of the compartments induced by pressing the compartment(s).

The infusion bag has a cover mounted thereon. The cover has a pair of pinch members that pinch at-least one of the plurality compartments. The pair of pinch members have engaging elements that engage each other to maintain the pinching state of the pinch members until the pinching state is released in response to an increase in the internal pressure of said at least one of the compartments so that the suspension portion can be used. The pair of pinch members cover a suspension portion in the pinching state for preventing the use of the suspension portion for suspending the infusion bag until said at least one easily peelable sealing partition is opened.

It is preferable that the cover mounted on the infusion bag be capable of being removed from the infusion bag when the pinching state is released, the suspension portion be formed in the body of the infusion bag, and the suspension portion be closed with the pair of pinch members in the pinching state.

In the cover mounted on the infusion bag, it is preferable that one of the pinch members be provided with a seat that fits into the suspension portion.

In the cover mounted on the infusion bag, it is preferable that the seat be provided with at least one engaging projection, and the other pinch member provided with at least one engaging hole that engages with said at least one engaging projection, so that the engaging projection(s) and the engaging hole(s) serve as the engaging elements.

In the cover mounted on the infusion bag, it is also preferable that one of the pinch members instead be provided with an engaging projection that fits into the suspension portion, and the other pinch member provided with an engaging hole that engages with the engaging projection, so that the engaging projection and the engaging hole serve as the engaging elements.

In the cover mounted on the infusion bag, the pair of pinch members are preferably swingably connected to each other.

In the cover mounted on the infusion bag, it is also preferable that one of the pinch members have fixing elements for fixing the one of the pinch members to the infusion bag, the suspension portion be formed in the other pinch member, and the latter pinch member be swingably connected to the former pinch member so that the latter pinch member can be opened and closed with respect to the former pinch member.

It is preferable that the cover mounted on the infusion bag further have a pair of press-preventing members extending from the pair of pinch members over at least said at least one compartment pinched between the pinch members, with the pair of press-preventing members being connected to the pair of pinch members via step portions so that the press-preventing members are disposed apart from each other.

In the cover mounted on the infusion bag, the pair of pinch members are preferably connected by a hinge portion.

Effects of the Device

By using the present device, the suspension portion is rendered inaccessible until the easily peelable partitioning seal portion is opened, i.e., before the medicaments are mixed, thereby making it impossible for the infusion bag to be hung, and thus preventing the administration of unmixed medicaments to a patient.

Best Mode for Achieving the Device

Hereinafter, embodiments of the object-suspending member cover of the present device are described with reference to the figures. In all the figures and embodiments, similar components are indicated with the same symbols.

A first embodiment is described with reference to FIGS. 1 and 2. FIG. 1 shows a plan view (a) and a side view (b) of an object-suspending member cover 10 according to this embodiment as attached to a multi-compartment infusion bag 1. FIG. 2 shows a plan view (a) and a side view (b) of the object-suspending member cover 10 according to this embodiment as removed from the multi-compartment infusion bag 1.

The multi-compartment infusion bag 1 is made of flexible transparent plastic. As shown in FIGS. 1 and 2, the multi-compartment infusion bag 1 has compartments 3 and 4 partitioned by an easily peelable partitioning seal portion 2, and a medicament outlet portion 5. The infusion bag 1 is provided with a suspension portion 6, formed on the side opposite to the medicament outlet portion 5, for suspending the bag 1. The configuration of the infusion bag 1 is such that when either or both of the compartments 3 and 4 are pressed, the internal pressure of the pressed compartment(s) is increased, and, in response to such an internal pressure increase, the easily peelable partitioning seal portion 2 is peeled, whereby the compartments 3 and 4 are communicated.

An object-suspending member cover 10 is mounted on the infusion bag 1 thus configured. The object-suspending member cover 10 has a pair of pinch members 11*a* and 11*b*. The pinch member 11*a* is provided with a seat 12 that fits into the suspension portion 6, and the seat 12 is provided with engaging projections 13*a*. The pinch member 11*b* is provided with engaging holes 13*b* that engage with the engaging projections 13*a*. Due to such a configuration, when the pinch members 11*a* and 11*b* are in the state of pinching, the engaging projections 13*a* and engaging holes 13*b* engage each other, whereby the pinching state of the pair of pinch members 11*a* and 11*b* is maintained. The engaging projections 13*a* and engaging holes 13*b* serve as the engaging elements of the present device. When the pinch members 11*a* and 11*b* are in the state of pinching, the seat 12 fits into the suspension portion 6, and displacement of the object-suspending member cover 10 relative to the multi-compartment infusion bag 1 can thus be prevented. Some displacement is allowable so long as the pair of pinch members 11*a* and 11*b* continue to pinch the compartment 4, and accordingly, the engaging projections 13*a* may extend directly from the pinch member 11*a* without the seat 12. The pair of pinch members 11*a* and 11*b* are swingably connected to each other by a hinge portion 17.

As examples of materials for the object-suspending member cover 10, plastics and metals can be mentioned. When plastic is used, the junction between the pinch member 11*a* and the pinch member 11*b* can be thin and thereby form the hinge portion 17, enabling the production to be simplified.

The following is a description of the use of the object-suspending member cover 10 thus configured.

First, as shown in FIG. 1, the object-suspending member cover 10 is mounted on the multi-compartment infusion bag 1 until the easily peelable partitioning seal portion 2 is opened. The object-suspending member cover 10 is mounted in such a manner that the pinch members 11*a* and lib thereof block the suspension portion 6. The pair of pinch members 11*a* and 11*b* pinch the compartment 4. The pinching state of the pinch members 11*a* and 11*b* is maintained, as described above, by the engagement of the engaging projections 13*a* with the engaging holes 13*b*.

Subsequently, the compartment 4 is pressed by hand or the like, so as to increase the internal pressure of the compartment 4 and thereby open the easily peelable partitioning seal portion 2, as shown in FIG. 2. Because the compartment 4 is pinched between the pinch members 11*a* and 11*b* of the object-suspending member cover 10, with such an internal pressure increase in the compartment 4, the pair of pinch members 11*a* and 11*b* are moved in separate directions. With such movement of the pinch members 11*a* and 11*b*, the engaging state of the engaging projections 13*a* with the engaging holes 13*b* is released, whereby the pinching state of the pinch members 11*a* and 11*b* is also released. Upon the removal of the object-suspending member cover 10 from the multi-compartment infusion bag 1, the suspension portion 6 that has been blocked with the pinch members 11*a* and 11*b* of the object-suspending member cover 10 is revealed and rendered accessible. The multi-compartment infusion bag 1 accordingly becomes capable of being suspended, and, after opening the medicament outlet portion 5 by insertion of an object or the like, a mixed medicament can be administered to a patient.

The above description of the first embodiment of the present device is not intended to limit the scope of the present device, and various modifications may be made without deviating from the scope of the device.

For example, although in the first embodiment the seat 12 fits into the suspension portion 6 to prevent displacement of the object-suspending member cover 10, and the engaging projections 13*a* on the seat 12 engage with the engaging holes 13*b* to maintain the pinching state of the pinch member 11*a* and 11*b*, it is also possible, as shown in FIG. 3, to form an engaging projection 13*a* that fits into the suspension portion 6, and so omit the seat 12. By forming an engaging projection 13*a* with a size that fits the suspension portion 6 in this way, displacement of the object-suspending member cover 10 can be prevented without a seat 12. Each engaging projection 13*a* preferably has a height about 1.1 to 3 times the thickness of the pinch member 11*b*. By adopting such a height, the pinch members can be prevented from being forcibly opened. Engagement of the engaging projection(s) 13*a* with the engaging hole(s) 13*b* may be made, for example, by friction between the outer wall of each engaging projection 13*a* and the inner wall of the corresponding engaging hole 13*b*, by convexo-concave engagement, by a tapered fitting, or like method.

Next, a second embodiment of the object-suspending member cover of the present device is described with reference to FIGS. 4 and 5. FIG. 4 shows a plan view (a) and a side view (b) of an object-suspending member cover 10 according to this embodiment, as attached to a multi-compartment infusion bag 1. FIG. 5 shows a plan view (a) and a side view (b) of the object-suspending member cover 10 as unfastened from the multi-compartment infusion bag 1.

As shown in FIGS. 4 and 5, unlike in the first embodiment described above, the multi-compartment infusion bag 1 has no suspension portion, but is provided with holes for passing engaging projections 13*a* and a headed engaging projection 14*a* of the object-suspending member cover 10, which are described hereinafter. The multi-compartment infusion bag 1 has otherwise the same configuration as in the first embodiment.

An object-suspending member cover 10 is mounted on the multi-compartment infusion bag 1 thus configured. The object-suspending member cover 10 has a pair of pinch members 11*a* and 11*b*, which are swingably connected with a hinge portion 17 so that the pinch members 11*a* and 11*b* can be opened and closed with respect to each other. One pinch member 11*a* has engaging projections 13*a* and a headed engaging projection 14*a*. The head of the headed engaging projection 14*a* is elastic. The other pinch member 11*b* has engaging holes 13*b* that engage the engaging projections 13*a*, and a suspension portion 16. The pinch member 11*b* includes a holder portion 15, which is separated from the pinch member 11*b* when the pinching state is released. The holder portion 15 has an engaging hole 14*b* that engages the headed engaging projection 14*a*. The headed engaging projection 14*a* and engaging hole 14*b* serve as the fixing elements of the present device.

The following is a description of the use of the object-suspending member cover 10 thus configured.

First, as shown in FIG. 4, the object-suspending member cover 10 is mounted on the multi-compartment infusion bag 1 until the easily peelable partitioning seal portion 2 is opened. For fitting the object-suspending member cover 10, the engaging projections 13*a* and the headed engaging projection 14*a* formed on one pinch member 11*a* are first inserted into the corresponding holes formed in the multi-compartment infusion bag 1. The object-suspending member cover 10 is then bent at the hinge portion 17 to move the other pinch member 11*b* close to the pinch member 11*a* and engage the engaging projections 13*a* and the headed engaging projection 14*a* with the engaging holes 13*b* and the engaging hole 14*b*, respectively. As a result, the pair of pinch members 11*a* and 11*b* holding the compartment 4 are maintained in a pinching state (see FIG. 4). At that time, the suspension portion 16 formed in the pinch member 11*b* is closed with the multi-compartment infusion bag 1.

When the compartment 4 is pressed with the hand or the like, the pair of pinch members 11*a* and 11*b* are moved in separate directions as in the first embodiment, so that the engaged state of the engaging projections 13*a* and the engaging holes 13*b* is released, and the pinching state of the pinch members 11*a* and 11*b* is also released (see FIG. 5). At that time, unlike in the first embodiment, the engaged state of the engaging hole 14*b* and the headed engaging projection 14*a* of the holder portion 15 of the other pinch member 11*b* is not released due to the presence of the head of the headed engaging projection 14*a*. Therefore, the holder portion 15 is separated from the pinch member 11*b* and maintains, together with the pinch member 11*a*, the pinched state of the multi-compartment infusion bag 1. Such a configuration prevents the object-suspending member cover 10 from being peeled from the multi-compartment infusion bag 1. The object-suspending member cover 10 is not limited to the configuration described above, and can be configured in any manner as long as one pinch member 11*a* of the object-suspending member cover 10 is not easily peeled from the multi-compartment infusion bag 1.

The other pinch member 11*b* is released from the engaged state and therefore can be opened in a direction separated from the pinch member 11*a*, thereby making the suspension portion 16 formed in the pinch member 11*b* usable.

As described above, according to the present device, the object-suspending member cover 10, which prevents the use of the suspension portions 6 and 16 until the easily peelable partitioning seal portion 2 is opened, is attached to the multi-compartment infusion bag 1. This prevents the multi-compartment infusion bag 1 from being hung until the medicaments contained therein are mixed, i.e., makes it necessary to mix the medicaments before hanging the multi-compartment infusion bag 1 to administer the medicaments to a patient. Therefore, administration of unmixed medicaments to patients can be reliably prevented.

The strength necessary for releasing the pinching state of the pinch members 11*a* and 11*b* can be adjusted by changing the sizes of the engaging projections 13*a* and the engaging holes 13*b*. The strength is preferably adjusted so that, when pressing the compartment 4, the pinching state of the pinch members is released substantially at the same time as or after the easily peelable partitioning seal portion 2 is opened.

The above description of the first and second embodiments of the present device is not intended to limit the scope of the present device, and various modifications may be made without deviating from the scope of the device.

For example, as shown in FIG. 6, the object-suspending member cover 10 can also be configured to further comprise a pair of press-preventing members 18*a* and 18*b* extending from the pair of pinch members 11*a* and 11*b* over the compartment 4. The pair of press-preventing members 18*a* and 18*b* are connected to the pair of pinch members 11*a* and 11*b* via step portions 19*a* and 19*b* so that the press-preventing members 18*a* and 18*b* are disposed apart from each other. The press-preventing members 18*a* and 18*b* thus configured prevent accidentally pressing the compartment 4. Further, depending on the material of the object-suspending member cover 10, the press-preventing members exhibit such effects that the pinching state of the pinch members can be smoothly released while making it difficult to forcibly open the pinch members. In the above configuration, it is preferable that the press-preventing members 18*a* and 18*b* are sufficiently wide to cover most of the surface of the compartment 4.

BRIEF DESCRIPTION OF DRAWINGS

FIG. 1 shows a plan view (a) and a sectional side view (b) of an object-suspending member cover according to a first embodiment of the present device, as attached to a multi-compartment infusion bag.

FIG. 2 shows a plan view (a) and a sectional side view (b) of the object-suspending member cover according to the first embodiment of the present device, as removed from the multi-compartment infusion bag.

FIG. 3 shows a plan view (a) and a sectional side view (b) of another object-suspending member cover according to the first embodiment of this device, as attached to a multi-compartment infusion bag.

FIG. 4 shows a plan view (a) and a sectional side view (b) of an object-suspending member cover according to a second embodiment of the present device, as attached to a multi-compartment infusion bag.

FIG. 5 shows a plan view (a) and a sectional side view (b) of the object-suspending member cover according to the second embodiment of the present invention, as unfastened from the multi-compartment infusion bag.

FIG. 6 shows a plan view (a) and a sectional side view (b) of an object-suspending member cover according to another embodiment of the present device, as attached to a multi-compartment infusion bag.

EXPLANATION OF NUMERALS

1 Multi-compartment infusion bag
2 Easily peelable partitioning seal portion
3, 4 Compartments
6, 16 Suspension portions
10 Object-suspending member cover
11 Pinch members
12 Seat
18 Press-preventing members
19 Step portions

The invention claimed is:

1. A cover for being mounted on a multi-compartment infusion bag comprising a plurality of compartments partitioned by at least one easily peelable partitioning seal portion which is opened in response to an increase in the internal pressure of at least one of the plurality of compartments induced by pressing said at least one of the plurality of compartments, the cover comprising:

a pair of pinch members that pinch at least one of the plurality of compartments, the pair of pinch members comprising engaging elements that engage each other to maintain a pinching state of the pair of pinch members until the pinching state is released in response to an increase in the internal pressure of said at least one of the compartments so that the suspension portion can be used, and covering a suspension portion in the pinching state for preventing the use of the suspension portion for suspending the infusion bag until said at least one easily peelable sealing partition is opened.

2. A cover according to claim 1, which can be removed from the infusion bag when the pinching state is released;

wherein the suspension portion is formed in a body of the infusion bag, and covered with the pair of pinch members in the pinching state.

3. A cover according to claim 2, wherein one of the pinch members has formed thereon a seat that fits into the suspension portion.

4. A cover according to claim 3, wherein the engaging elements comprise:

at least one engaging projection formed on the seat, and at least one engaging hole that engages with said at least one engaging projection formed in the other pinch member.

5. A cover according to claim 1, wherein the engaging elements comprise:

an engaging projection that fits into the suspension portion formed on one of the pinch members, and an engaging hole that engages the engaging projection formed in the other pinch member.

6. A cover according to claim 1, wherein the pair of pinch members are swingably connected to each other.

7. A cover according to claim 1, wherein:

one of the pinch members has fixing elements for fixing the one of the pinch members to the infusion bag; and the other pinch member has the suspension portion formed thereon and is swingably connected to the one of the pinch members so that the other pinch member can be opened and closed with respect to the one of the pinch members.

8. A cover according to claim 1, further comprising press-preventing members each extending from each of the pair of pinch members over at least said at least one compartment pinched between the pinch members;

wherein each of the press-preventing members is connected to each of the pair of pinch members via a step portion so that the press-preventing members are disposed apart from each other.

9. A cover according to claim 1, wherein the pair of pinch members are connected to each other by a hinge portion.

10. A multi-compartment infusion bag comprising a plurality of compartments partitioned by at least one easily peelable partitioning seal portion which is opened in response to an increase in the internal pressure of at least one of the plurality of compartments induced by pressing said at least one of the plurality of compartments, and having a cover mounted thereon, the cover comprising:

a pair of pinch members that pinch at least one of the plurality of compartments, the pair of pinch members comprising engaging elements that engage each other to maintain a pinching state of the pair of pinch members until the pinching state is released in response to an increase in the internal pressure of said at least one of the compartments so that the suspension portion can be used, and covering a suspension portion in the pinching state for preventing the use of the suspension portion for suspending the infusion bag until said at least one easily peelable sealing partition is opened.

11. An infusion bag according to claim 10, wherein:

the cover can be removed from the infusion bag when the pinching state is released, and the suspension portion is formed in a body of the infusion bag, and covered with the pair of pinch members in the pinching state.

12. An infusion bag according to claim 11, wherein one of the pinch members has formed thereon a seat that fits into the suspension portion.

13. An infusion bag according to claim 12, wherein the engaging elements comprise:

at least one engaging projection formed on the seat, and at least one engaging hole that engages with said at least one engaging projection formed in the other pinch member.

14. An infusion bag according to claim 10, wherein the engaging elements comprise:

an engaging projection that fits into the suspension portion formed on one of the pinch members, and an engaging hole that engages the engaging projection formed in the other pinch member.

15. An infusion bag according to claim 10, wherein the pair of pinch members are swingably connected to each other.

16. An infusion bag according to claim 10, wherein:

one of the pinch members has fixing elements for fixing the one of the pinch members to the infusion bag; and the other pinch member has the suspension portion formed thereon and is swingably connected to the one of the pinch members so that the other pinch member can be opened and closed with respect to the one of the pinch members.

17. An infusion bag according to claim 10, wherein:

the cover further comprises press-preventing members each extending from each of the pair of pinch members over at least said at least one compartment pinched between the pinch members, and each of the press-preventing members is connected to each of the pair of pinch members via a step portion so that the press-preventing members are disposed apart from each other.

18. An infusion bag according to claim 10, wherein the pair of pinch members are connected to each other by a hinge portion.

* * * * *